United States Patent [19]

Whittlinger

[11] Patent Number: 5,223,628
[45] Date of Patent: Jun. 29, 1993

[54] PROCESS FOR MAKING HIGH SOLIDS FABRIC SOFTENERS USING LOW AMOUNTS OF SOLVENTS AND NO SIDE REACTIONS

[75] Inventor: David E. Whittlinger, Janesville, Wis.

[73] Assignee: Sherex Chemical Company, Inc., Dublin, Ohio

[21] Appl. No.: 790,131

[22] Filed: Nov. 7, 1991

Related U.S. Application Data

[63] Continuation of Ser. No. 474,347, Feb. 20, 1990, abandoned.

[51] Int. Cl.$^5$ ................... C07C 209/00; C07D 233/24
[52] U.S. Cl. ..................... 548/349.1; 554/1; 554/103; 554/52; 554/223; 564/204; 564/215; 564/291; 564/292; 564/294; 564/296; 252/8.6; 252/8.75; 252/8.8
[58] Field of Search ........ 252/8.6, 8.75, 8.8; 548/349.1; 554/1, 103, 52, 223; 564/204, 215, 291, 292, 294, 296

[56] References Cited

U.S. PATENT DOCUMENTS

| | | | |
|---|---|---|---|
| 2,474,202 | 6/1949 | Rust | 260/404.5 Q |
| 2,583,772 | 1/1952 | Gunderson | 260/404.5 Q |
| 4,237,064 | 12/1980 | Reck | 260/459 |
| 4,238,373 | 12/1980 | Hardy et al. | 252/542 |

FOREIGN PATENT DOCUMENTS

| | | |
|---|---|---|
| 0004108 | 9/1979 | European Pat. Off. |
| 0008839 | 3/1980 | European Pat. Off. |
| 0132138 | 1/1985 | European Pat. Off. |
| 0281975 | 9/1988 | European Pat. Off. |
| 0345495 | 12/1989 | European Pat. Off. |

*Primary Examiner*—Richard L. Raymond
*Attorney, Agent, or Firm*—Scully, Scott, Murphy and Presser

[57] ABSTRACT

A process is disclosed for making substantially solvent free quaternary ammonium compounds using fatty acids, amines and quaternizing agents without side reactions that would produce esters of fatty acids. A relatively small amount of a water-alcohol solvent is used in the quaternizing reaction after which a fatty acid is added and the solvent removed by sparging and/or vacuum.

9 Claims, No Drawings

PROCESS FOR MAKING HIGH SOLIDS FABRIC SOFTENERS USING LOW AMOUNTS OF SOLVENTS AND NO SIDE REACTIONS

This application is a continuation of application Ser. No. 474,347, filed on Feb. 2, 1990, now abandoned.

BACKGROUND OF THE INVENTION

1. Field of the Invention

The invention relates to a process for making substantially solvent free quaternary ammonium compounds using fatty acids, amines and quaternizing agents without side reactions such as those reactions that would produce esters of fatty acids. A more fluid product is obtained than the ester-containing softener blends used for dryer softener sheets. Ordinarily quaternization of the amine takes place in the presence of the fatty acid and the quaternizing agent, resulting in the formation of the ester of the fatty acid which makes the resultant product viscous and difficult to handle. By employing the method of the present invention, in which a relatively small amount of a water-alcohol solvent is used in the quaternizing reaction after which a fatty acid is added and the solvent removed, a product is obtained which is ready to be flaked or powdered and can be used as a fabric softener, lubricant, hair conditioner, in the manufacture of aqueous dispersions and the like.

2. Brief Description of the Prior Art

The preparation of quaternary ammonium compounds is usually conducted in stainless steel or glass-lined equipment to which a tertiary amine is charged and a solvent. Flammable solvents such as isopropyl alcohol are generally used although mixtures of isopropyl alcohol and water sometimes are employed or water alone is used. Flammable solvents are undesirable because they are a fire hazard and special handling procedures are required when they are used. In many applications, these solvents have to be stripped from the mixture when the reaction is completed because the ultimate use of the product is in a solventless or solid form.

After the reactants are loaded into the reactor they are heated to a temperature of about 50° to about 100° C. after which a quaternizing reagent is added. In some instances an exotherm is produced as a result of the quaternizing reaction and the reactor and its contents have to be cooled. The rate of addition of the quaternizing agent can also be controlled in order to minimize or eliminate the exotherm. As noted previously, in some instances, the solvent, if any is employed in the quaternizing reaction is stripped from the quaternary ammonium compound obtained since some commercial uses for the compounds are in solventless systems. Additionally, bulk shipments of quaternary ammonium compounds with solvents adds to transportation costs which is another reason to remove the solvents.

It is also known in the prior art that when water alone is used as the solvent a gelatinous sticky mass is obtained from which the water is difficult to remove. When alcohol is used as the solvent for the quaternizing reaction the products obtained are not as difficult to handle as when water is used, however, when used, it presents not only a fire hazard but also an environmental problem if released to the air. The combinations of water and alcohol have been used for several years in quaternization reactions and this solvent mixture generally is removed by either sparging and/or by applying a vacuum to the quaternary ammonium compound thus produced which contains the solvents. These processes, although commercially employed are not entirely satisfactory primarily because the mixture of solvents with the quaternary ammonium compound and other reactants and by-products is viscous to the point where solvent removal can be difficult.

The largest use for quaternary ammonium compounds is as a fabric softener and presently accounts for more than about three quarters of the total market for these material. Some fabric softeners are supplied as a liquid dispersion of from about 3% to about 10% by weight of the quaternary ammonium compound which is adapted to be added during the rinse cycle of a commercial or home laundering operation. Another significant fabric softening application is the utilization of quaternary ammonium compounds in combination with a substrate such as a nonwoven fabric or a polymeric foam such as a polyurethane foam, this substrate so treated being added to a fabric dryer such as a clothes dryer while the fabric or clothes are still damp. The quaternary ammonium compound is formulated usually with a fatty acid or ester which promotes the transfer of the quaternary ammonium compound from the nonwoven or porous polymeric substrate to the fabric or clothes.

Quaternary ammonium compounds are now being added to both solid and liquid laundry detergent compositions so that the quaternary ammonium compound can be incorporated as a fabric softener during the wash cycle of fabrics or clothes. The most successfully utilized quaternary ammonium compounds in this last respect are the dimethyl (dihydrogenated tallow) ammonium chlorides or methyl sulfates. Other quaternary ammonium compounds such as imidazolines and amidoamine quaternaries are also used.

Quaternary ammonium compounds are also used to manufacture organomodified clays which may be added to drilling muds utilized in drilling oil wells, the organomodified clay providing improved lubrication and rheological properties of the drilling muds. These organoclays are also employed as thixotropic agents in plastisols, organosols, paints and other protective coatings, grease additives, foundry additives, cosmetics, resins and printing inks. The most common quaternary ammonium compounds employed in this regard are methyldi(hydrogenated tallow) benzylammonium chloride, dimethyldi(hydrogenated tallow) ammonium chloride and dimethyl(hydrogenated tallow) benzylammonium chloride.

Quaternary ammonium compounds are also employed as disinfectants, e.g. bactericides or bacteristats, the most common of which is the quaternary ammonium compound of benzylchloride and a dimethylalkylamine, the alkyl group having from about 12 to about 16 carbon atoms as well as trimethyl alkyl ammonium chlorides where the alkyl group is a long chain alkyl such as an octadecyl group. Additionally, dimethyl-dicoconut-oil fatty ammonium chlorides are also effective bactericides especially against anaerobic bacteria which are sulfate reducers that are found in oil wells, these bacteria causing severe corrosion problems and plugging of formations which this type of quaternary ammonium compound can minimize or eliminate. Additionally, these quaternary ammonium compounds effective against anaerobic bacteria are also effective in removing oil from sand stone formations in oil wells and provide a two-fold effect of functioning not only as a bactericide but also in promoting so-called secondary recovery of oil.

An additional use of quaternary compounds is in hair treatment because of the antistatic effects obtained with such compounds, as well as the increased wetting which promotes improvements in both wet and dry combing or brushing and improves luster and feel. The most commonly used quaternary ammonium compounds in this respect are trimethylalkylammonium chloride, pentaethoxystearylammonium chloride, dimethylstearylbenzylammonium chloride and dimethyldialkylammonium chlorides.

It is therefore an object to overcome these and other difficulties encountered in the prior art.

It is also an object of the present invention to provide a method for manufacturing a mixture of quaternary ammonium compounds with a fatty acid inter allia which can be used in fabric softening applications. It is also an object of the present invention to provide such mixtures.

It is a further object of the present invention to provide a method for making a mixture of a quaternary ammonium compound from which the solvents such as mixtures of water and alcohol can be readily removed by conventional methods such as sparging and/or vacuum.

It is also an object of the present invention to provide such a mixture which is relatively fluid so that the removal of solvents such as mixtures of alcohols and water is readily achieved by sparging and/or vacuum.

It is also an object of the invention to provide such mixtures with low amounts of solvents but are nonetheless relatively fluid so that the solvents such as water and alcohol can be readily removed by sparging and/or vacuum.

It is also an object of the invention to provide a method for making such mixtures for use as fabric softeners.

It is a further object of the present invention to provide a composition comprising such mixtures with low amounts of solvents such as water and alcohol that lend themselves to the easy removal of such solvents by sparging and/or vacuum.

It is a further object of the invention to provide mixtures of quaternary ammonium compounds with a fatty acid that can be employed in any or all of the foregoing applications.

These and other objects have been achieved according to the present invention which will be further understood in view of the following description and claims.

SUMMARY OF THE INVENTION

It has been found that a highly functional mixture of a quaternary ammonium compound, and a fatty acid can be obtained that is substantially free of fatty acid esters, amine salts and solvents by a quaternization reaction in which an amine is quaternized by a quaternizing agent in the presence of relatively small amounts of water and an alcohol until the quaternization reaction is substantially complete. A first mixture of a quaternary ammonium compound, alcohol and water is obtained after which a fatty acid is added to the first mixture to obtain a second mixture that is relatively fluid. This is followed by removing the alcohol and water as a vapor from the second mixture to thereby obtain a quaternary ammonium compound in combination with such fatty acid, the combination being substantially free of fatty acid esters, amine salts and the water and alcohol.

The prior art method uses 3-5 wt % water and 2-3 wt % isopropanol to facilitate pumping and transportation. The process according to the invention uses less than 3% water and less than 2% alcohol (e.g. isopropanol). The fatty acid is added which thins the product whereby solvents may be removed and the product remains fluid at lower temperatures. This allows for lower storage temperatures than quaternaries alone or with the solvent mixtures of the prior art and also lower storage than quaternaries blended with the traditional esters used in the known prior art methods.

DETAILED DESCRIPTION

The tertiary amine employed according to the invention has the formula:

where R, $R^1$ and $R^2$ can be any of the following in combination (1) linear or branched chain saturated or unsaturated hydrocarbon groups having up to about 22 carbon atoms;

(2) a lower hydroxy alkyl group;

(3) an alkyl amido alkylene group of the formula:

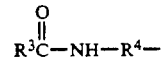

where $R^4$ is lower alkylene and $R^3$ is any of R, $R^1$ or $R^2$;

(4) lower alkoxy group;

(5) poly(oxyloweralkylene) group;

so that at least one of R, $R^1$ or $R^2$ is one of said linear or branched chain aliphatic saturated or unsaturated hydrocarbon groups;

or said tertiary amine is an imidazoline of the formula:

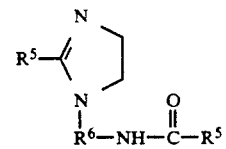

where $R^5$ is a linear or branched chain, aliphatic saturated or unsaturated hydrocarbon group having up to about 22 carbon atoms and $R^6$ is a lower alkylene group;

said quaternizing agent being known in the art and which will produce a quaternary ammonium compound having an anion $A^-$. Generally these anions are those having the formula $R^7_{(a-b)}X$;

where $R^7$ is a lower alkyl group or cyclo lower alkyl group such as benzyl, cyclohexylmethyl, tolyl, xylyl, naphthylmethyl, and X is chlorine, iodine, bromine, sulfate, methyl sulfate, carbonate, phosphate, borate group, where (a) is equal to the valence of X and (b) is from 1 to the valence of X and are based on quaternizing agents having the formula $R^7_aX$.

Examples of tertiary amines that can be employed include:

distearyl methyl amine, dihydrogenated tallow methyl amine,
ditallow methyl amine,
dimethyl hydrogenated tallow amine,
dimethyl coco amine,
distearyl ethoxyethyl amine,
stearyl bis-hydroxyethyl amine,
stearyl bis (polyethoxy ethanol) amine,
bis (tallowamidoethyl) 2-hydroxyethyl amine,
bis (tallowamidoethyl) 2-hydroxylpropyl amine,
1-hydrogenated tallow amido ethyl -2-hydrogenated tallow imidazoline,
1-ethylene bis (2 tallow, 1 methyl, imidazolinium) dimethyl amino propyl tallow amido-amine and hydrogenated tallow hydroxyethyl imidazoline, Examples of Quaternizing Agents that can be employed include:
dimethyl sulfate,
diethyl sulfate,
methyl chloride,
methyl bromide and
benzyl chloride.

Said fatty acid is a linear or branched chain aliphatic saturated or unsaturated fatty acid having from about 12 to about 22 carbon atoms based on coconut oil, vegetable oils, seed oils, animal fats and fish oils;

The quaternary ammonium compound thus obtained has the formula:

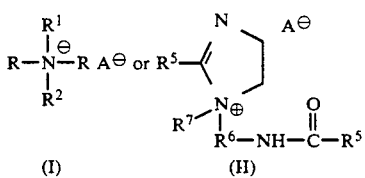

(I)    (II)

where $A^-$ is an anion based on $R^7_{(a-b)}X$ or equivalent anions known in the quaternary ammonium compound art;

and the fatty acid ester has the formula:

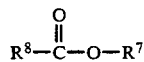

where $R^8$ is a linear or a branched chain aliphatic saturated or unsaturated hydrocarbon group having from about 11 to about 21 carbon atoms.

As used throughout this specification the terms lower alkoxy, lower alkylene and lower alkyl are intended to include compounds having up to about 3 or about 4 carbon atoms including the various isomeric configurations thereof e.g. t-butyl, i-butyl, i-propyl and the like and the various mixtures thereof whether such mixtures of such groups contain components having one, or two, or three or four carbon atoms or more and also where such groups individually or in combination are in any of their isomeric forms.

Equivalent amines (including imidazolines), quaternizing agents, fatty acids and surface active agents are disclosed in U.S. patents to Marschner U.S. Pat. No. 4,859,456; Caswell et al., U.S. Pat. No. 4,857,213; Demangeon et al., U.S Pat. No. 4,851,141 and Mermelstein et al., U.S Pat. No. 4,844,824 all of which are incorporated herein by reference.

Sparging is generally conducted by passing an inert gas such as nitrogen, (carbon dioxide etc.)through the mixture. Combinations of inert gases may also be used.

One or more valved gas inlets are placed in the reactor in which the quaternary ammonium compound is formed, the openings being below the level of the reactants in the reactor and preferably at the bottom of the reactor. Similarly, a pipe or a plurality of pipes can be inserted through the top of the reactor down to the reactants so that the openings thereof are positioned below the surface of the reactants preferably towards the bottom of the reactants and the reactor. The sparging gas is then introduced at a sufficient flow and pressure so that the sparging gas introduced into the reactants can sweep the reacting mixture and pull the water and alcohol from the reactants as the gas exits the reactants at the surface in the form of bubbles.

The solvents may also be removed by vacuum, for example under reduced pressures of from less than 760 mm to about 2 mm of mercury and especially from about 200 mm to about 10 mm of mercury either before, during or after sparging. Any combination or sequences of sparging and vacuum stripping of solvents may be employed.

The reactants in combination with the fatty acid, during sparging and vacuum treatment may be held at a temperature from about 50° to about 120° C. and especially from about 80° to about 100° C.

The amine, water and alcohol are added to the reactor and heated to about 140° F. prior to the addition of the quaternization reaction and preferably a slight nitrogen purge is initiated at this time and prior to the addition of the quaternizing agent. In conducting the reaction, the amine is present in a slight stoichiometric excess e.g. from about 0.005 to about 5% excess and especially from about 0.01 to about 1% excess and the quaternizing agent is added incrimentally so as to maintain a reaction temperature of from about 50° to about 100° C. and especially from about 60° to about 90° C. It is standard practice in the art to add the quaternizing agent incrementally since the quaternization reaction is generally exothermic and the temperature of the reaction can be controlled by this type of addition. The progress of the reaction is followed so that when the amount of free amine has stabilized at from about 1 to about 2% by weight (that point in the reaction when the quaternization reaction has been substantially completed) the fatty acid is added. After addition of the fatty acid, the mixture is heated to anywhere from about 80° to about 110° C. and especially from about 90° to about 100° C. and the solvents (water and alcohol) are removed either by sparging, vacuum stripping or any combination of the two processes in any order, combination or sequence of sparging and vacuum stripping steps.

In conducting the quaternization reaction, sufficient alcohol is added so that there is from about 0.1 to about 5% and especially from 1 to about 3% by weight of alcohol present and water is similarly added so that there is from about 0.25 to about 5% and especially from about 1 to about 4% by weight of water present. The amount of water and alcohol in terms of weight percent is calculated on the basis of amine, quaternizing agent, water, alcohol and fatty acid in the reaction mixture. The alcohol is a lower alkanol such as those alcohols having up to about five carbon atoms, especially the mono-hydroxy alcohols and includes the various isomers thereof such as isopropyl alcohol, isobutyl alcohol, t-butyl alcohol and various combinations thereof including azeotropes of such alcohols or such alcohols and water.

The amount of quaternary ammonium compound and fatty acid obtained in the mixture after the solvents have been removed from the reaction are from about 10 to about 90 weight percent and especially from about 55 to about 75 weight percent of quaternary ammonium compound and from about 90 to about 10 weight percent and especially from about 25 to about 45 weight percent by weight of fatty acid. The amine and quaternizing agent are reacted in sufficient ratios and the fatty acid is added afterwards to the quaternary ammonium compound thus obtained in sufficient amounts so as to obtain the foregoing ratios after the water and alcohol have been removed.

The alcohol and water are sufficiently removed from the quaternary ammonium compound mixed with the fatty acid so that a mixture of quaternary ammonium compound and fatty acid is obtained in amounts from about 95% to about 100% and especially about 98% to about 100% i.e. substantially all of the water and alcohol solvents are removed. Stated otherwise the mixture may contain anywhere from about 2% to about 5% of the water and alcohol solvent down to that point where substantially all or all of the water and alcohol solvent is removed.

In one embodiment, the method of the invention is preferably practiced so that the quaternary ammonium compound that is obtained has the structural formula (I) wherein at least one of R, $R^1$ and $R^2$ is a branched chain or linear aliphatic saturated or unsaturated hydrocarbon group having from about 12 to about 22 carbon atoms, preferably saturated, and especially those based on hard tallow acids (i.e. hydrogenated tallow fatty acids) and the balance, if any of the aforesaid R, $R^1$ and $R^2$ groups is a lower alkyl group and $R^7$ is a lower alkyl group. In another embodiment X is a sulfate group.

The invention also relates to a mixture of the various quaternary ammonium compounds as described above in combination with the fatty acids in the amounts and ratios as described previously.

The invention also relates to a fabric softening article of manufacture comprising a fabric softening amount of any of the mixtures as described herein operatively associated with a substrate that will release such mixture to a fabric under fabric softening conditions encountered in a fabric or clothes dryer and includes the use of any of the aforesaid mixtures in a fabric softening relationship with a nonwoven or woven fiber or a polymeric open-celled or substantially open-celled foam substrate, such combination being prepared in a manner well known in the art. The mixture is employed in an amount from about 0.1 to about 10 gms on a 9"×11" sheet and especially about 1 to about 3 gms on a 9"×11" sheet.

The various polymeric foams that are employed in this respect comprise polyurethane foams as well as any of the art known equivalent foams.

Additionally, the invention is directed to a fabric cleaning composition comprising a detergent in combination with a fabric softening amount of any of the mixtures described herein. These detergents can be any of the art known anionic, cationic, nonionic or amphoteric synthetic detergents or wetting agents that are well known in the art or a soap i.e. the reaction product of a fatty acid with a alkaline hydroxide that is water soluble e.g. fatty acid reaction products of sodium, potassium or ammonium hydroxides or amines or the art known equivalents thereof.

Shampoos may also be formulated according to the invention with such detergents and a hair conditioning amount of the quaternary ammonium compound and fatty acid mixtures of the present invention.

These surfactants are further described in Kirk-Othmer, *Encyclopedia of Chemical Technology*, 3rd Edition Vol. 22 pp. 332-432 which is incorporated herein by reference. Some specific detergents that are especially suitable in this regard include:

alkyl benzene sulfate,
sodium lauryl ether sulfate,
nonyl phenyl ethoxylates and
alkyl alcohol ethoxylates.

The mixture of the invention is incorporated into the detergents or soaps (whether solid or liquid) by blending in a manner well known in the art. The amount of the mixture employed is any where from about 1 to about 50 and especially from about 2 to about 30 wt. % based on the quaternary ammonium compound and the active components of the detergent or soap i.e. the component of the detergent or soap that has both organophilic and hydrophilic groups.

The following example is illustrative.

The method of the invention as well as a mixture obtained according to this method is examplified by the preparation of a mixture employing the following components in the indicated amounts.

| Components | M.W. | Moles | % by Wt. |
| --- | --- | --- | --- |
| Dihydrogenated Tallow-Methyl-Amine | 523 | 1.00 | 53.52 |
| Dimethyl Sulfate | 126 | 0.98 | 12.98 |
| Water | | | 3.0 |
| Ethanol | | | 2.0 |
| Stearic Acid | | | 28.5 |

The amine, water and alcohol are charged to a reactor and heated to 140° F. A nitrogen purge was used over the surface of the reactants in the reactor to minimize contact of the reactants with air. The dimethylsulfate was charged at a rate to maintain the temperature of the reactants at 140°-180° F. When the percentage of free amine has stabilized at 1.0-2.0 weight percent the stearic acid is added and mixed. The mixture thus obtained is heated to 200° F. after which the water and ethanol are removed by means of nitrogen sparging and/or vacuum stripping.

The foregoing method produced a reaction mixture which was analyzed by NMR analysis showing that it had the following components:

| | Weight Percent |
| --- | --- |
| Quaternary Ammonium compound | 67 |
| Fatty Acid | 33 |

Although the invention has been described by reference to some embodiments, it is not intended that the novel method or the mixture obtained thereby as well as the fabric softening article of manufacture and the detergent containing a fabric softening amount of the mixture be limited thereby but that certain embodiments are intended being included as falling within the broad scope and spirit of the foregoing disclosure and the following claims.

I claim:

1. A method for making a mixture of a quaternary ammonium compound and a fatty acid which is substantially free of solvents, fatty acid esters and amine salts by reacting a tertiary amine and a quaternizing agent in the presence of a solvent based on an alcohol and water to obtain a first mixture of a quaternary ammonium compound, said alcohol and said water, adding a fatty acid to said first mixture to obtain a second mixture that is relatively fluid and removing said alcohol and said water as a vapor to thereby obtain said quaternary ammonium compound and said fatty acid that is substantially free of solvents, fatty acid esters and amine salts:

where in said quaternizing reaction said amine is present in a slight stoichiometric excess based on said quaternizing agent, said alcohol is present in an amount from about 0.1 to about 5% by weight, said water is present in an amount from about 0.25 to about 5% by weight, said amounts of alcohol and water being based on the total amount of amine, quaternizing agent, alcohol, water and fatty acid;

said tertiary amine having the formula:

wherein R, R¹ or R² are:

(1) a linear or branched chain aliphatic saturated or unsaturated hydrocarbon group having up to about 22 carbon atoms;

(2) a hydroxy lower alkyl group;

(3) an alkyl amide alkylene group of the formula;

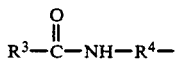

where R⁴ is lower alkylene and wherein R³ is (1), (2), (4), or (5);

(4) a lower alkoxy group;

(5) a poly(oxyloweralkylene) group;

so that at least one of R, R¹, R² is one of said hydrocarbon groups or one of said hydroxy lower alkyl groups;

or said tertiary amine is an imidazoline of the formula;

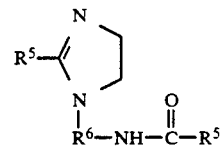

wherein R⁵ is a linear or branched chain aliphatic saturated or unsaturated hydrocarbon group having up to about 22 carbon atoms and R⁶ is a lower alkylene group;

said quaternizing agent being capable of producing a quaternary ammonium compound having anions A⁻;

wherein said fatty acid is a linear or branched chain saturated or unsaturated fatty acid having from about 12 to about 22 carbon atoms;

said quaternary ammonium compound having the formula:

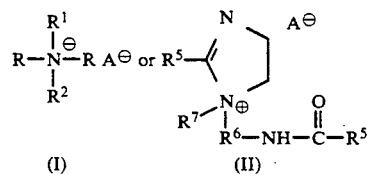

(I)  (II)

2. The method of claim 1 where said second mixture is subjected to sparging with a gas at temperatures of from about 80° C. to about 100° C. to remove any of said water or alcohol.

3. The method of claim 1 where said second mixture is subjected to a vacuum to remove any of said water or alcohol.

4. The method of claim 2 where said second mixture, is also subjected to a vacuum to remove any of said water or said alcohol.

5. The method of claim 4 where said quaternary ammonium compound is (I) and wherein at least one of said R, R¹ and R² groups is a branched chain or linear, aliphatic saturated or unsaturated hydrocarbon group having from about 12 to about 22 carbon atoms and the balance, if any, of said R, R¹ and R² groups is a lower alkyl group.

6. The method of claim 4 where said amine is a dihydrogenated tallow methyl amine and said quaternizing agent is a dialkyl sulfate and said fatty acid is stearic acid.

7. The method of making a fabric softening article of manufacture comprising making a mixture of a quaternary ammonium compound and a fatty acid according to the method of claim 4, and operatively associating a fabric softening amount of said mixture with a fabric under fabric softening conditions.

8. The method of claim 7 where said substrate is a non-woven fabric.

9. The method of claim 8 where said substrate is a polymeric foam.

* * * * *

UNITED STATES PATENT AND TRADEMARK OFFICE
CERTIFICATE OF CORRECTION

PATENT NO. : 5,223,628
DATED : June 29, 1993
INVENTOR(S) : David E. Whittlinger

It is certified that error appears in the above-indentified patent and that said Letters Patent is hereby corrected as shown below:

On the Title Page, Section [63]: "Feb. 20," should read as --Feb. 2,--

Column 10, lines 23-26, Claim 1: "$\begin{array}{c} R^1 \\ | \ominus \\ R-N-R \\ | \\ R^2 \end{array}$"

--$\begin{array}{c} R^1 \\ | \oplus \\ R-N-R^7 \\ | \\ R^2 \end{array}$--

Signed and Sealed this

Twelfth Day of April, 1994

Attest:

BRUCE LEHMAN

*Attesting Officer*    *Commissioner of Patents and Trademarks*